United States Patent [19]

Ávár et al.

[11] 3,963,737

[45] June 15, 1976

[54] 1,3-DIHYDROCARBYL-PYRAZOLE COMPOUNDS AS STABILIZERS FOR ORGANIC MATERIALS

[75] Inventors: Lajos Ávár, Binningen; Kurt Hofer, Munchenstein, both of Switzerland

[73] Assignee: Sandoz Ltd., Basel, Switzerland

[22] Filed: July 2, 1975

[21] Appl. No.: 592,369

[30] Foreign Application Priority Data
July 9, 1974 Switzerland............ 9418/74

[52] U.S. Cl.................. 260/299; 260/45.75 N; 260/310 R
[51] Int. Cl.$^2$............... C07F 15/04; C08K 5/33
[58] Field of Search................ 260/242, 299

[56] References Cited
UNITED STATES PATENTS

| | | | |
|---|---|---|---|
| 3,256,291 | 6/1966 | Swiatoslaw | 260/299 |
| 3,265,705 | 8/1966 | Mahler | 260/299 |

*Primary Examiner*—Donald B. Moyer
*Attorney, Agent, or Firm*—Gerald D. Sharkin; Richard E. Vila; Joseph J. Borovian

[57] ABSTRACT

1,3-Dihydrocarbyl-pyrazole compounds, having a 5-hydroxyl group in free or nickel salt form, characterized by a ketoxyimino group bound directly to the 4-position of the pyrazole ring through the ketoxyimino functional carbon atom, which are useful as stabilizers of organic materials against the adverse effects of ultraviolet light.

8 Claims, No Drawings

1,3-DIHYDROCARBYL-PYRAZOLE COMPOUNDS AS STABILIZERS FOR ORGANIC MATERIALS

IMPROVEMENTS IN OR RELATING TO ORGANIC COMPOUNDS

The present invention relates to derivatives of pyrazole compounds which are useful as stabilizers of organic materials against the adverse effects of ultraviolet light.

Accordingly, the present invention provides 1,3-dihydrocarbyl-pyrazole compounds, having a 5-hydroxyl group in free or nickel salt form, characterized by a ketoxyimino group bound directly to the 4-position of the pyrazole ring through the ketoxyimino functional carbon atom.

For the avoidance of doubt, by the term ketoxyimino group is meant a group of the formula

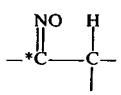

the carbon atom *C being the ketoxyimino functional carbon atom.

As will be appreciated, the various substituents on the pyrazole ring and any substituents on these substituents should be selected so as not to affect the U.V. stabilizng properties or stability of the compounds. The selection of such substituents forms part of the general knowledge in the U.V. stabilizer art.

A preferred class of pyrazole compounds from the above class of such compounds are those of formula I,

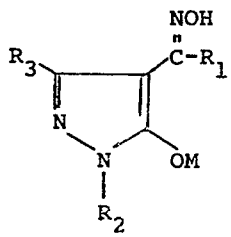

I in which
R$_1$ is C$_5$–C$_{17}$alkyl; phenyl-C$_1$–C$_4$alkyl, of which the phenyl radical is unsubstituted or substituted by up to 4 substituents selected from 1 or 2 hydroxyl and 1 or 2 C$_1$–C$_6$alkyl radicals; phenyl, unsubstituted or substituted by up to 3 substituents selected from 1 to 3 halogen atoms, a hydroxyl radical 1 or 2 C$_1$–C$_8$alkyl radicals, 1 or 2 C$_1$–C$_8$alkoxy radicals and a phenyl radical; or 2-furyl, 3-furyl, 2-thienyl, 3-thienyl, 2-benzothienyl or 3-benzothienyl, each of which heterocyclic radicals is unsubstituted or substituted by 1 or 2 halogen atoms or by a C$_1$–C$_4$alkyl radical,
each of R$_2$ and R$_3$, independently, is C$_1$–C$_8$alkyl or phenyl, the latter unsubstituted or substituted by up to 4 substituents selected from 1 or 2 halogen atoms and 1 or 2 C$_1$–C$_4$alkyl radicals,
and M is hydrogen or an equivalent of nickel.

In the above definition of formula I, it is to be understood that any alkyl radical, either as such or as part of an alkoxy or phenylalkyl radical, may be straight or branched chain when containing 3 or more carbom atoms, and may be primary or secondary. Any such radical containing 4 or more carbon atoms may additionally be tertiary.

Halogen means fluorine, chlorine or bromine, of which chlorine is prefered.

When R$_1$ is alkyl, this preferably contains 6 to 17 carbon atoms, more preferably 8 to 15 carbon atoms, and most preferably 9, 11 or 15 carbon atoms.

When R$_1$ is an optionally substituted phenyl radical, this is preferably unsubstituted. However, when substituted, it preferably bears up to 3 substituents selected from a chlorine atom, a hydroxyl radical in the para position, 1 or 2 C$_1$–C$_4$alkyl racicals and 1 or 2 C$_1$–C$_4$alkoxy radicals, more preferably bears a single C$_1$–C$_4$alkyl substituent, and most preferably bears a tert.-butyl radical.

Preferably R$_1$ is alkyl or optionally substituted phenyl, more preferably alkyl.

When R$_2$ or R$_3$ is alkyl, this preferably contains 1 to 4 carbon atoms, and most preferably is methyl.

When R$_2$ or R$_3$ is an optionally substituted phenyl radical, this is preferably unsubstituted. However, when substituted, it preferably bears 1 or 2 C$_1$–C$_4$alkyl radicals.

Independently, R$_2$ preferably is alkyl or unsubstituted phenyl, more preferably unsubstituted phenyl, and R$_3$ preferably is alkyl or unsubstituted phenyl, more preferably alkyl, particularly methyl.

M is preferably an equivalent of nickel.

Thus a preferred class of compounds of formula I is constituted by compounds of formula I$a$

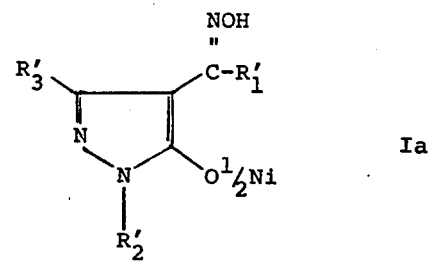

Ia in which
R$_1$' is C$_6$–C$_{17}$alkyl or phenyl, unsubstituted or substituted by up to 3 substituents selected from a chlorine atom, a p-hydroxyl radical, 1 or 2 C$_1$–C$_4$alkyl radicals and 1 or 2 C$_1$–C$_4$alkoxy radicals,
and each of R$_2$' and R$_3$', independently, is C$_1$–C$_4$ alkyl or phenyl, unsubstituted or substituted by 1 or 2 C$_1$–C$_4$alkyl radicals.

A preferred class of compounds of formula I$a$ is constituted by compounds of formula I$b$,

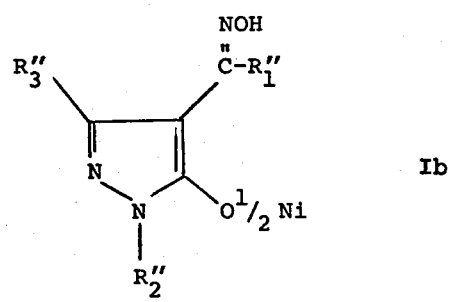

Ib in which $R_1''$ is $C_8$–$C_{15}$alkyl or phenyl, unsubstituted or substituted by a $C_1$–$C_4$alkyl radical, and each of $R_2''$ and $R_3''$, independently, is methyl or unsubstituted phenyl.

A preferred class of compounds of formula Ib is constituted by compounds of formula Ic.

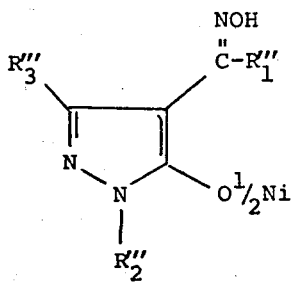

Ic in which $R_1''$ is $C_8$–$C_{15}$alkyl or phenyl, unsubstituted or substituted by a $C_1$–$C_4$alkyl radical, $R_2'''$ is unsubstituted phenyl, and $R_3'''$ is methyl.

The invention further provides a process for the production of a pyrazole compound of the invention, as described above, which comprises reacting the corresponding pyrazole compound, wherein the 4-position is occupied by a keto group directly bound to that position by the carbonyl carbon atom, with hydroxylamine in free base or acid addition salt form, and when required, converting the free 5-hydroxyl group into the nickel salt form.

An example of the above process of the invention is a process for the production of a compound of formula I, as defined above, which comprises reacting a compound of formula II,

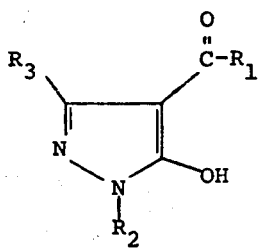

II in which $R_1$, $R_2$ and $R_3$ are as defined above, with hydroxylamine in free base of acid addition salt form, and, when required, converting the free 5-hydroxyl group into the nickel salt form.

In the process of the invention, suitable salts of hydroxylamine which may be used instead of the free base form include the hydrochloride, hydrobromide, acetate, sulphate and tartrate.

The reaction conditions use for the process may be those conventionally employed for converting a carbonyl group to its oxime derivative, and, in the case where the free 5-hydroxyl group is to be converted into the nickel salt form, for effecting such a conversion.

The compounds of formula II used as the starting materials in the particular example of the process of the invention given above may be produced in conventional manner from known starting materials or from starting materials produced by analogous processes to those for producing the known starting materials.

The present invention further provides a method of stabilizing an organic material against the degradative effects of ultraviolet light comprising "treating" the organic material with a pyrazole compound of the invention, as described above. By the term "treating," as used herein, is meant either incorporating into the body of the organic material or surface coating the organic material, in a manner known per se.

Suitable organic materials which benefit from the method of the present invention include such natural substances as rubber, cellulose, wool and silk, and plastics materials, in particular polyolefins, e.g., polyethylene and polypropylene, polyesters, polyvinyl chloride, polymethyl methacrylates, polypropylene oxide, polyphenylene oxides, polyurethanes, polystyrene, cellulose acetobutyrate, polyamides, e.g., nylon, polyacrylonitrile, polycarbonate, copolymers of the aforementioned polymers, and ABS-terpolymers.

Preferably the pyrazole compounds of the present invention are used for stabilizing polyethylene, polypropylene, polyesters, in particular polyethylene terephthalate, polyvinyl chloride, polycarbonate, polyamide, polyurethanes, cellulose acetobutyrate, polystyrene, polyacrylonitrile, copolymers of styrene and acrylonitrile and of styrene and butadiene, ABS-terpolymers and terpolymers of acrylic ester, styrene and acrylonitrile.

According to a first embodiment of the method of the present invention, the pyrazole compound is intimately mixed with the organic material to be treated, e.g., a plastics material such as polypropylene, preferably in granular form, in a kneader or other suitable mixing device, after which the material is extruded.

According to a second embodiment of the method of the present invention, particularly suited to the stabilization of polymeric or copolymeric materials, the pyrazole compound is mixed with the appropriate monomer(s) and/or prepolymer before polymerization of copolymerization is effected.

After the polymerization or copolymerization the product has the compound distributed therethrough, and it may thereafter be extruded, moulded or otherwise formed into final shape.

The organic materials may also be treated with other additives besides the pyrazole compounds of the invention to improve their properties, e.g., other stabilizers or co-stabilizers, e.g., against the degradative effects of oxygen, heat and/or ultraviolet light.

The amount of stabilizing pyrazole compound employed in the method of the present invention will natuarally depend on several factors, including the mode of application, the particular compound employed and the nature of the organic material to be treated. However, satisfactory results are generally obtained when the amount of compound employed is in the range 0.01 to 5%, preferably 0.05 to 1%, of the weight of the organic material to be treated.

The present invention further provides an organic material whenever treated according to the method of the present invention. Stabilized organic materials according to the present invention may exist in solid form, e.g., foam plastics, sheets, rods, coatings, plates, foils, films, strips, apes, loops, filaments, fibres, granules, powders and other working forms, or in liquid form, e.g., solutions, emulsions and dispersions.

The present invention is illustrated by the following Examples, in which the parts and percentages are by weight. The indicated structures of the compounds are determined by microanalysis and infra-red spectroscopy.

EXAMPLE 1

27.8 Parts of 1-phenyl-3-methyl-4-benzoyl-pyrazol-5-one, 7.0 parts of hydroxylamine hydrochloride and 16.0 parts of triethylamine in 100 parts of methanol are heated under reflux for 15 hours. The methanol is then distilled off, 300 parts of water are added to the remaining brown oil, and the mixture is stirred for 15 minutes, whereupon precipitation occurs. The resulting precipitate is collected by filtration, washed with water and crystallized from methanol. Produced is a pale yellow powder, m.p. 167°–169°C, of formula

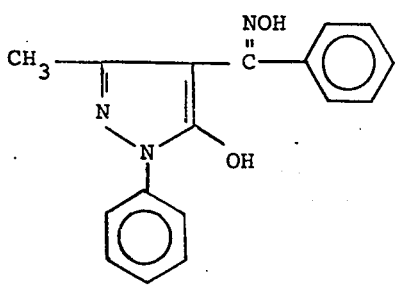

EXAMPLE 2

By a similar procedure to that described in Example 1, using 1-phenyl-3-methyl-4-(4-tert.-butyl-benzoyl)-pyrazol-5-one in place of the corresponding 4-benzoyl compound, the compound of formula,

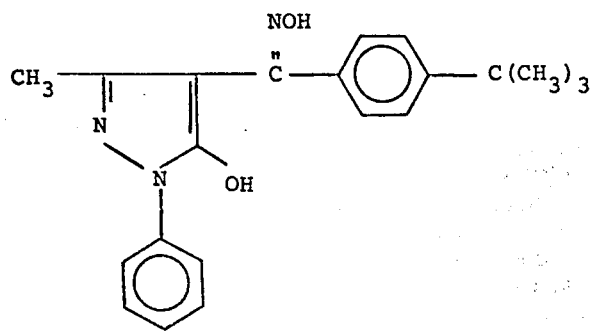

m.p. 172°–173°C, is produced.

EXAMPLE 3

To a solution of 15.5 parts of the compound whose production is described in Example 2 in 100 parts of methanol, boiling under reflux, are added 3.74 parts of nickel acetate tetrahydrate. A green precipitate is immediately produced, and this is collected by filtration at room temperature, washed with methanol and then water, and dried. Produced is a bright green powder, m.p. >250°C, of formula,

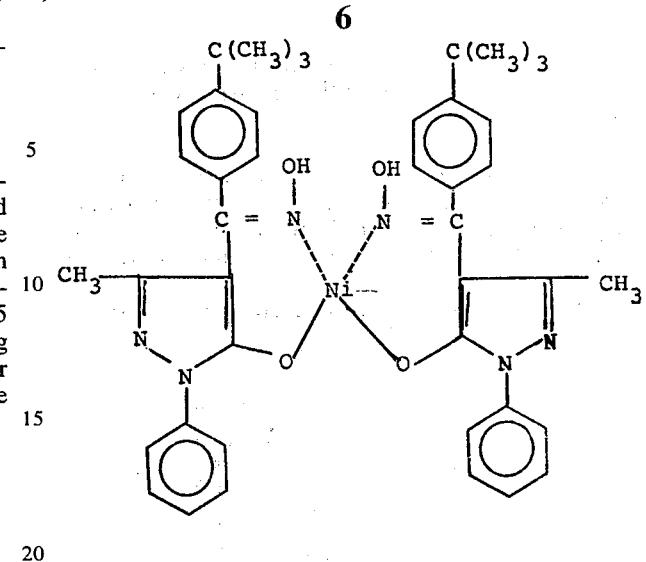

EXAMPLES 4 to 12

By a similar procedure to that described in Examples 1 and 3 using appropriate starting materials, the compounds in the following table are produced.

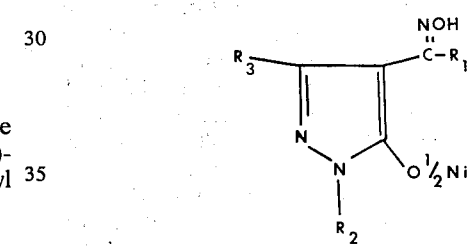

| Example No | $R_1$ | $R_2$ | $R_3$ | m.p.°C |
|---|---|---|---|---|
| 4 | phenyl | phenyl | $CH_3$ | >200 |
| 5 | n-$C_{15}H_{31}$ | " | " | ~130 |
| 6 | n-$C_{11}H_{23}$ | " | " | ~150 |
| 7 | n-$C_9H_{19}$ | " | " | ~160 |
| 8 | phenyl | p-methyl-phenyl | " | >200 |
| 9 | " | p-chloro-phenyl | " | >200 |
| 10 | " | phenyl | phenyl | >200 |
| 11 | p-methoxy-phenyl | " | " | >200 |
| 12 | thienyl | " | " | >200 |

APPLICATION EXAMPLE

The compound of Example 1 is incorporated into 200 times its weight of non-stabilized polypropylene at 180°C in a roller mill, and the mixture is pressed into sheets of 0.3 mm thickness. These sheets are tested for their resistance agains u.v. light by the De La Rue method of the climate test. The test is carried out at 40°C, at 75% relative humidity and with strong ventilation using 16 Philips sunlamps and 16 Philips blacklamps, and satisfactory results are obtained.

In a similar manner the compound of Example 3 in non-stabilized polypropylene and the compound of Example 4 in non-stabilized polyvinyl chloride are tested in the climate test, similarly satisfactory results being obtained.

Satisfactory results are also obtained when polyethylene, polyethylene tetraphthalate, polyamide-6, polyurethane, polystyrene and ABS-terpolymers are used as the substrates.

What is claimed is:

1. A 1,3-dihydrocarbyl-pyrazole compound, having a 5-hydroxyl group in nickel salt form, characterized by a ketoxyimino group bound directly to the 4-position of the pyrazole ring through the ketoxyimino functional carbon atom.

2. A compound according to claim 1, of the formula,

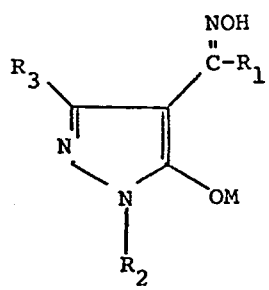

in which
R₁ is C₅–C₁₇alkyl; phenyl-C₁–C₄alkyl, of which the phenyl radical is unsubstituted or substituted by up to 4 substituents selected from 1 to 2 hydroxyl and 1 or 2 C₁–C₆alkyl radicals; phenyl, unsubstituted or substituted by up to 3 substituents selected from 1 to 3 halogen atoms, a hydroxyl radical, 1 or 2 C₁–C₈alkyl radicals, 1 or 2 C₁–C₈alkoxy radicals and a phenyl radical; or 2-furyl, 3-furyl, 2-thienyl, 3-thienyl, 2-benzothienyl or 3-benzothienyl, each of which heterocyclic radicals is unsubstituted or substituted by 1 or 2 halogen atoms or by a C₁–C₄alkyl radical, each of R₂ and R₃, independently, is C₁–C₈ alkyl or phenyl, the latter unsubstituted or substituted by up to 4 substituents selected from 1 or 2 halogen atoms and 1 or 2 C₁–C₄alkyl radicals,
and M is an equivalent of nickel.

3. A compound according to claim 2, of the formula,

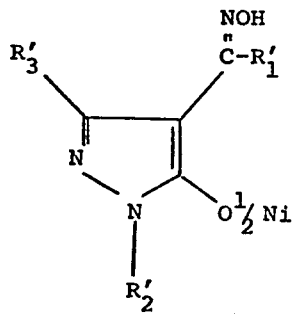

in which
R₁' is C₆–C₁₇alkyl or phenyl, unsubstituted or substituted by up to 3 substituents selected from a chlorine atom, a p-hydroxyl radical, 1 or 2 C₁–C₄alkyl radicals and 1 or 2 C₁–C₄alkoxy radicals, and each of R₂' and R₃', independently, is C₁–C₄ alkyl or phenyl, unsubstituted or substituted by 1 or 2 C₁–C₄alkyl radicals.

4. A compound according to claim 3, of the formula,

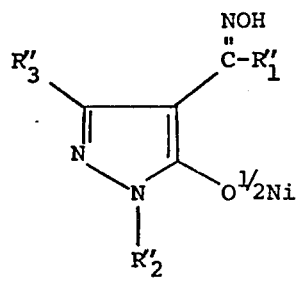

in which
R₁'' is C₈–C₁₅alkyl or phenyl, unsubstituted or substituted by a C₁–C₄alkyl radical,
and each of R₂'' and R₃'', independently, is methyl or unsubstituted phenyl.

5. A compound according to claim 4, of the formula,

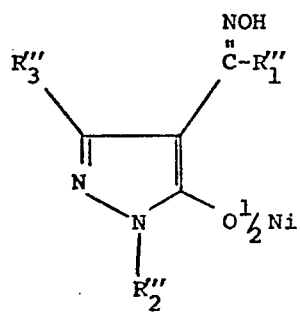

in which
R₁''' is C₈–C₁₅alkyl or phenyl, unsubstituted or substituted by a C₁–C₄allkyl radical,
R₂''' is unsubstituted phenyl,
and R₃''' is methyl.

6. The compound according to claim 5, of the formula,

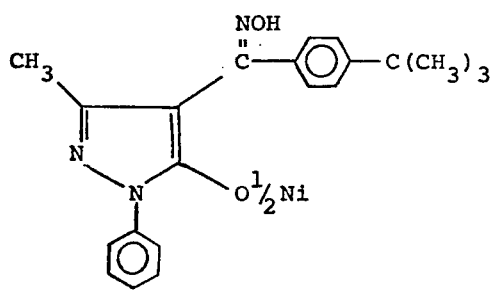

7. The compound according to claim 5, of the formula,
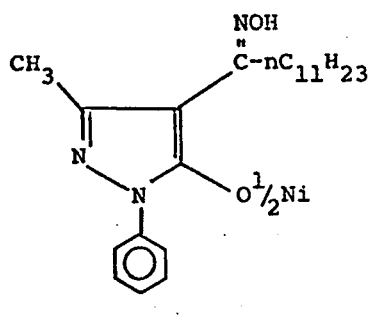
8. The compound according to claim 5, of the formula,
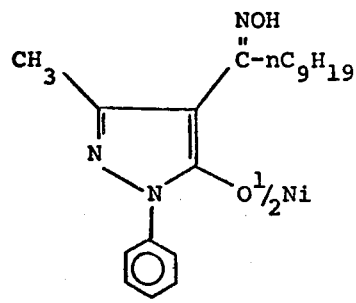
* * * * *